United States Patent [19]

Serres

[11] Patent Number: 5,316,681
[45] Date of Patent: May 31, 1994

[54] METHOD OF FILTERING BODY FLUID USING A RINSE CHAMBER BAG

[75] Inventor: Margaret Serres, Wauconda, Ill.

[73] Assignee: Baxter International Inc., Deerfield, Ill.

[21] Appl. No.: 972,702

[22] Filed: Nov. 6, 1992

[51] Int. Cl.⁵ .................... B01D 37/00; B01D 61/00
[52] U.S. Cl. ................... 210/645; 206/221; 210/767; 604/89; 604/406; 604/410
[58] Field of Search .............. 210/767, 645, 791, 797; 604/406, 410, 416, 85, 4, 87, 5, 89; 206/219, 221

[56] References Cited

U.S. PATENT DOCUMENTS

| | | | |
|---|---|---|---|
| 3,257,072 | 6/1966 | Reynolds | 604/410 |
| 4,507,114 | 3/1985 | Bohman et al. | 604/111 |
| 4,591,357 | 5/1986 | Sneider | 604/416 |
| 4,608,043 | 8/1986 | Larkin | 604/87 |
| 4,810,378 | 3/1989 | Carmen et al. | 210/206 |
| 4,857,190 | 8/1989 | Wada et al. | 210/232 |
| 4,915,848 | 4/1990 | Carmen et al. | 210/749 |
| 4,943,287 | 7/1990 | Carmen | 604/408 |
| 4,975,186 | 12/1990 | Wada et al. | 210/232 |
| 4,985,153 | 1/1991 | Kuroda et al. | 210/782 |
| 4,994,056 | 2/1991 | Ikeda | 604/410 |
| 4,997,083 | 3/1991 | Loretti et al. | 206/219 |
| 5,089,146 | 2/1992 | Carmen et al. | 210/782 |
| 5,092,996 | 3/1992 | Spielberg | 210/232 |
| 5,100,564 | 3/1992 | Pall et al. | 210/782 |
| 5,102,407 | 4/1992 | Carmen et al. | 604/410 |
| 5,102,408 | 4/1992 | Hamacher | 604/410 |
| 5,104,788 | 4/1992 | Carmen et al. | 435/2 |
| 5,114,004 | 5/1992 | Isono et al. | 206/222 |
| 5,257,985 | 11/1993 | Puhl | 604/410 |

*Primary Examiner*—Matthew O. Savage
*Attorney, Agent, or Firm*—Bradford R. L. Price; Paul C. Flattery; Robert M. Barrett

[57] ABSTRACT

The present invention provides an improved method and container for filtering a body fluid. The method comprises the steps of isolating a volume of solution in a first chamber of a container; collecting a body fluid in a second chamber of a container; passing the body fluid through a filter; and rinsing the filter with an isolated volume of solution.

12 Claims, 2 Drawing Sheets

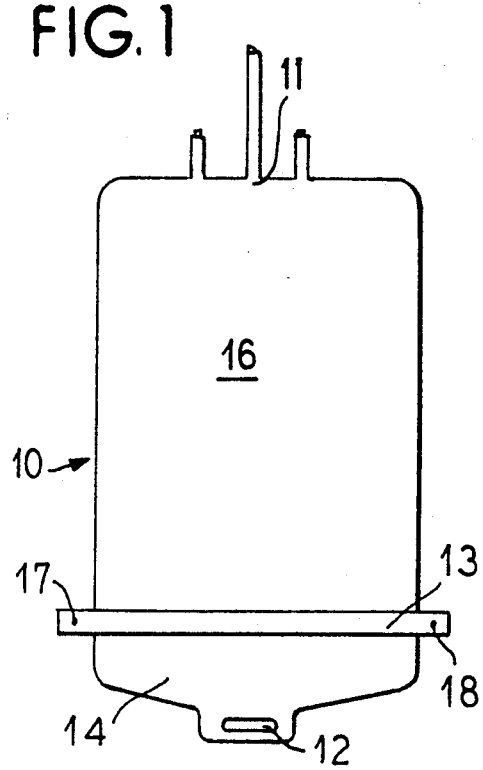
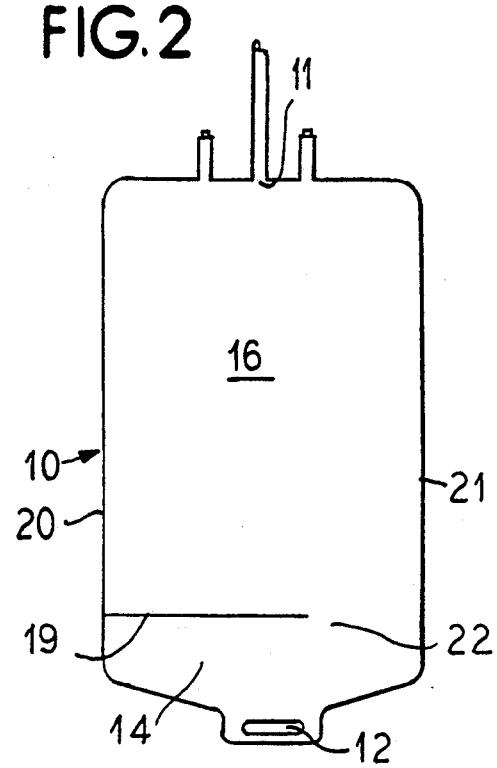
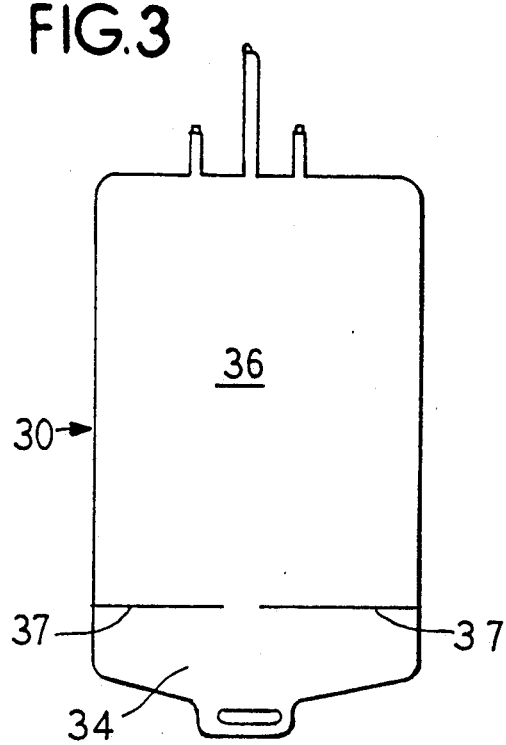
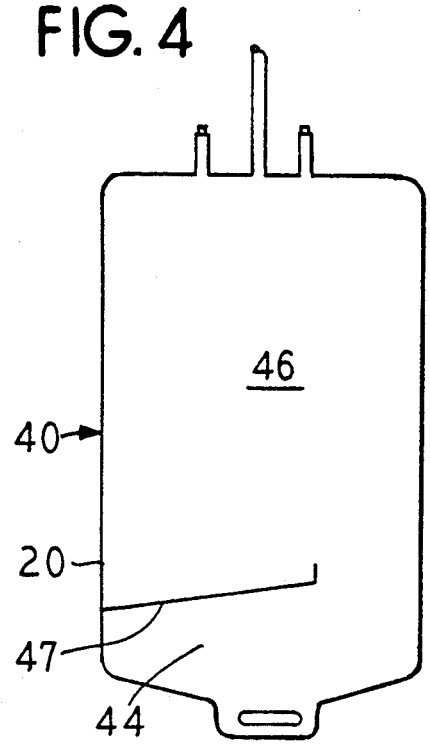

METHOD OF FILTERING BODY FLUID USING A RINSE CHAMBER BAG

BACKGROUND OF THE INVENTION

The present invention relates generally to the collection and filtration of body fluids. More specifically, the present invention relates to the leukodepletion of red blood cells.

In a variety of therapies, such as transfusion and transplants, body fluids, especially blood components, such as red blood cells, platelets, plasma, and bone marrow, are infused from one or more individuals into a patient. Three principal indications for the transfusion of a blood component exist: 1) deficiency in oxygen-carrying red blood cells; 2) deficiency in hematologic factors related to blood clotting, including platelets or protein coagulation factors; and 3) deficiency in plasma volume.

Patients requiring a transfusion do not receive whole blood, but, rather receive the specific component required to overcome the clinical deficiency. For example, patients undergoing chemotherapy or radiation therapy require primarily platelets and to a lesser degree red blood cells. Bone marrow or other organ transplant and dialysis patients generally require only red blood cells.

Some blood components, such as leukocytes, are generally unwanted because they are not relevant to the therapeutic effects of oxygen-carrying red blood cells, platelets, or plasma. Leukocytes also have been implicated as increasing the risks associated with blood transfusions for their role in alloimmunization to HLA antigens and post transfusion infection by acting as virus carrying cells. Thus, a filtering process is used to remove leukocytes in approximately 10% of the transfused blood components, although this percent may increase in the future. This process is called leukodepletion.

In collecting blood, commonly an anticoagulant is added to the whole blood collected from the donor. Whole blood can be separated into its components. The separated components can be placed in storage containers. For example, red blood cells are collected and stored in containers that include a storage solution such as Adsol ® available from Baxter Healthcare of Deerfield, Ill.

As previously stated, it may be desirable to remove the leukocytes from, for example, red cells before they are transfused. A typical leukodepletion filtering process comprises passing the blood component that is housed in a container through a filter designed to capture leukocytes without damaging the blood components. To improve recovery of the blood component, a storage solution is used to rinse any remaining blood components through the filter.

The current process utilizes separate containers to store both the blood component and the subsequent rinse solution. Various concerns exist with the current approach. For instance, using multiple containers increases manufacturing costs and is burdensome for the personnel. In addition, a possibility of contamination exists when solutions are housed in multiple containers. Furthermore, a disadvantage of the present system is that typically, blood components will remain on the walls of the storage container reducing yield.

Therefore, a need exists for an improved method for the leukofiltration of blood components, as well as a container useful in performing such method.

SUMMARY OF THE INVENTION

The present invention provides an improved method for filtering body fluid and containers useful in performing same. Specifically, the present invention provides a method which uses a container that simultaneously holds a body fluid to be filtered and a rinse solution. Moreover, the present invention provides a system for the leukofiltration of blood components.

Pursuant to the method of the present invention a body fluid is filtered through a method that comprises the step of isolating a volume of solution in a first chamber of a container. Then, a body fluid is collected in a second chamber of the container. The body fluid is then passed through a filter. The container and filter are then rinsed with the isolated volume of solution.

In a preferred embodiment, the method removes leukocytes from a blood component. The method effectively improves the recovery of the blood component during the leukodepletion filtering process.

The present invention also provides a container which allows for the simultaneous storage a body fluid and a rinse solution. The container comprises first and second walls which define an interior therebetween. The walls include an internal seal terminating at a location to create an opening between the first and second chamber that is closable by an external separating means that forces the internal sides together. The first chamber is designed to isolate a rinse solution, whereas, the second chamber contains a body fluid.

In an embodiment, the external separating means is a clamp.

An advantage of the present invention is that it provides an improved method for leukofiltration.

Furthermore, an advantage of the present invention is that it provides a method that substantially decreases manufacturing and supply costs.

Moreover, an advantage of the present invention is that it provides a container that simultaneously holds a body fluid to be filtered as well as a rinse solution, eliminating the need for multiple containers.

Still further, an advantage of the present invention is that the same rinse solution rinses the container and filter, eliminating the need for multiple rinse solutions.

Further, an advantage of the present invention is that it eliminates the use of multiple containers and also eliminates the possibility of contamination associated with the use of multiple containers.

Additional features and advantages of the present invention are described in, and will be apparent from, the detailed description of the presently preferred embodiments and from the drawings.

BRIEF DESCRIPTION OF THE DRAWINGS

FIG. 1 illustrates a perspective view of an embodiment of a container of the present invention for collecting body fluid to be filtered.

FIG. 2 illustrates the container of FIG. 1 without the external clamp.

FIG. 3 illustrates a perspective view of a further embodiment of a container of the present invention for collecting body fluid to be filtered.

FIG. 4 illustrates a perspective view of yet another embodiment of a container of the present invention for collecting body fluid to be filtered.

DETAILED DESCRIPTION OF PRESENTLY PREFERRED EMBODIMENTS

Figure 5:
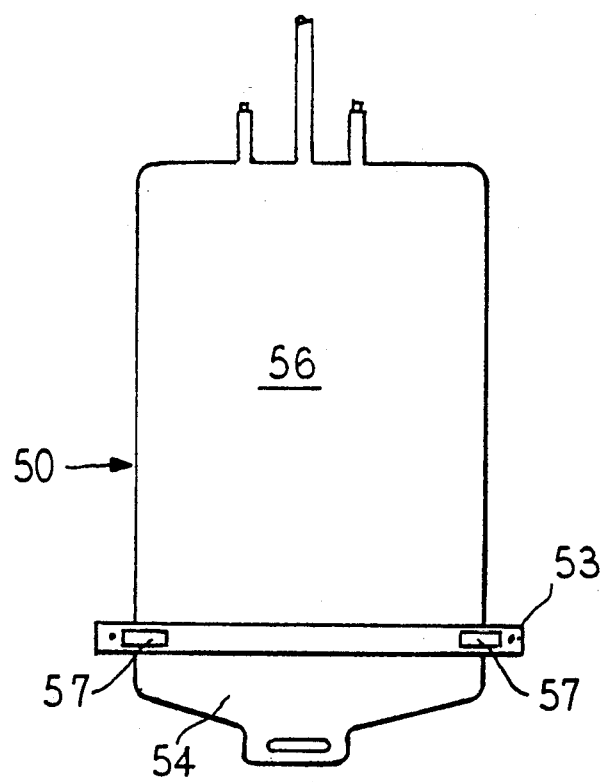
FIG. 5 illustrates a perspective view of an embodiment of a container of the present invention for collecting body fluid to be filtered, with an external clamp.

The present invention provides an improved method for filtering body fluids and containers useful in performing the same. Although the preferred embodiment discussed below is with reference to the filtering of red blood cells, the present invention can be used to filter other body fluids.

Referring now to the Figures and specifically to FIGS. 1 and 2, a container 10 is illustrated. The container 10 is designed to receive and house red blood cells. The container is formed of a heat sealable polymeric material, such as polyvinyl chloride. The container 10 is sealed to form a bag like structure and includes at least one tube or port 11 in fluid communication with the interior of container 10. The tube 11 allows for the collection of red blood cells as well as a rinse solution and a storage solution.

Pursuant to the present invention, the container 10 is divided into at least two chambers 14 and 16. To this end, as illustrated in FIG. 2, the interior of the container includes a seal 19. The seal 19, or seal line, extends from a side wall 20 across the interior of the container, but terminates before side wall 21. Therefore, an opening 22 providing fluid communication between the chambers 14 and 16 is provided. This allows a fluid, and preferably the rinse solution, to be isolated in chamber 14.

To isolate a fluid in chamber 14, illustrated in FIG. 1, an external clamp 13 can be used to force the sides of container 10 together. This isolates chamber 14 from 16. Although, in the illustrated embodiment, the clamp 13 extends across an entire width of the container 10, this may not be necessary to seal off aperture 22. Likewise, any clamp can be used such as a hemostat. In the illustrated embodiment, the clamp comprises two aluminum bars including internal pads that are secured together by screws 17 and 18.

In use, the container 10 will be filled with a volume of a rinse solution. Because a clamp will not be in place, chamber 14 will be filled through aperture 22 with the rinse solution. When red cells are to be stored in the container, the isolated volume will be a storage solution. A solution that can be used as the rinse and storage solution pursuant to the present invention includes ADSOL ®, available from Baxter Healthcare Corporation, Deerfield, Ill. In an embodiment, chamber 14 isolates approximately 20 ml of a rinse solution.

After the chamber 14 has been filed with the appropriate volume of storage solution, the aperture 22 is then closed by using the clamp 13. A further volume of storage solution ® can then be added to the container, as desired, for the red cells to be housed therein. Red blood cells may now be collected and housed in the container 10.

Prior to use of the red cells, pursuant to the present invention, they are subject to leukofiltration. A variety of leukocyte filters are available. Examples of leukocyte filters include the Sepacell ® R-500 filter available from Asahi Corp., Tokyo, Japan and the RC-100 for blood filtration available from Pall Biomedical Corp., East Hills, N.Y.

The container 10 is suspended by hanger hole 12. The tube 11 is opened and the red blood cells contained in the chamber 16 are allowed to flow through the tube 11 and the filter. To rinse out any remaining body fluid in chamber 16 as well as the filter, clamp 13 is released thereby causing the rinse solution contained within chamber 14 to flow into the second chamber 16. The rinse solution effectively removes any remaining red blood cells from the walls of the container 10. Further, it rinses the red blood cells through the filter, resulting in an increased recovery of the body fluid.

In an embodiment that has been found to function satisfactorily, the seal 19 extends across the container 10 perpendicular to side wall 20 and defines an opening approximately 0.5 inches from the side 22 of container 10. The seal 19 is positioned approximately 0.75 inches from the end of the container 10. This created a chamber 14 that can house at least 20 ml of storage solution.

Of course, it will be appreciated that a number of different seal structures can be used. FIGS. 3 and 4 illustrate further embodiments of containers of the present invention illustrating various embodiments of an internal seal positioned within the body of the containers.

Referring to FIG. 3, a container 30 is illustrated. The container 30 is substantially similar to the container 20 illustrated in FIGS. 2 and 3. The container 30 includes a seal 37. However, unlike seal 19 of container 10, the seal 37 has an opening within its center. The seal 37 when used with a clamp partially isolates a volume of rinse solution in chamber 34.

FIG. 4 illustrates another embodiment of the container 40. Similar to the container 10 of FIGS. 1 and 2, the container 40 includes a seal 47 extending across the container 40. However, the seal 47 extends in an upward angle across container 40. Further, the seal 47 includes a vertical portion at its end. The vertical seal increases the area upon which a clamp can be positioned, thereby reducing the potential for leakage. The seal 47 partially isolates a volume of rinse solution in chamber 44.

In an embodiment, the seal 47 extends across the container 40 defining an opening approximately 0.5 inches from the side of container 40. The seal 47 extends initially from the side wall 20 at a position approximately 0.75 inches from the end of the container 40.

Although a clamp is not illustrated in FIGS. 3-4, each container will be used with a clamp positioned across the seal. The clamp acts in conjunction with the internal seal to completely isolate a volume of solution in chambers 34 and 44, respectively.

If desired, the seal can extend across the entire interior of the container and a frangible seal can be used. Prior to filtration, the frangible seal would be ruptured, providing communication between the two chambers.

It is also possible that the container does not include a seal. Rather, the clamp would alone isolate a volume of fluid and divide the container into two chambers.

FIG. 5 illustrates a further embodiment of the container 50. If when the container 50 is clamped the solution contained in chamber 54 leaks near the side seals, seals 57, as illustrated in FIG. 5, can be placed along the side seals. The clamp 53 is then positioned across the seals 57. Such seals 57 decrease the possibility of leakage. Such seals 57 can be created with a Sebra sealer.

Pursuant to the present invention, an improved method for filtering a body fluid is provided. Pursuant to the method, a volume of rinse solution is isolated in chamber 14. Then, an external separating means is used to isolate the rinse solution in chamber 14.

Next, a body fluid is collected in chamber 16 of container 10. The body fluid is then passed through a filter. After passing the body fluid through the filter, the external separating means is released thereby causing the isolated volume of solution to flow into chamber 16. The rinse solution effectively removes any remaining body fluid left in the container. Further, the same rinse solution removes any body fluid remaining on the filter.

It should be understood that various changes and modifications to the presently preferred embodiments described herein will be apparent to those skilled in the art. Such changes and modifications can be made without departing from the spirit and scope of the present invention and without diminishing its attendant advantages. It is therefore intended that such changes and modifications be covered by the appended claims.

I claim:

1. A method for filtering a body fluid comprising the steps of:
    isolating a volume of solution in a first chamber of a container;
    collecting a body fluid in a second chamber of the container;
    passing the body fluid through a filter; and
    rinsing the filter with the isolated volume of solution.

2. The method of claim 1 wherein an external separating means is used to isolate the solution.

3. The method of claim 2 wherein the external separating means is a clamp.

4. The method of claim 2 wherein the container is rinsed by releasing the separating means thereby causing the isolated volume of solution to flow into the second chamber.

5. The method of claim 1 wherein the body fluid is a blood component.

6. The method of claim 1 further including the step of providing an internal seal extending across a portion of the container for partially isolating the volume of rinse solution.

7. A method for filtering leukocytes from a blood component comprising the steps of:
    isolating a volume of solution in a first chamber of a container;
    collecting the blood component in a second chamber of a container;
    passing the blood component through a leukocyte filter; and
    causing the isolated volume of solution to rinse the leukocyte filter.

8. The method of claim 7 wherein the blood component is red blood cells.

9. The method of claim 8 wherein the solution is a red blood cell storage solution.

10. The method of claim 7 including the step of providing the container with a seal to isolate the volume of solution.

11. The method of claim 10 wherein the seal does not extend across the entire width of the container.

12. The method of claim 7 wherein an external means is used to at least partially isolate the volume of solution.

* * * * *